(12) United States Patent
Mayberry (10) Patent No.: US 11,026,715 B2
(45) Date of Patent: Jun. 8, 2021

(54) CHEST CAVITY SUCTION MEDICAL APPARATUS AND METHOD

(71) Applicant: John Mayberry, Eagle, ID (US)

(72) Inventor: John Mayberry, Eagle, ID (US)

( * ) Notice: Subject to any disclaimer, the term of this patent is extended or adjusted under 35 U.S.C. 154(b) by 503 days.

(21) Appl. No.: 15/719,036

(22) Filed: Sep. 28, 2017

(65) Prior Publication Data

US 2019/0090898 A1 Mar. 28, 2019

(51) Int. Cl.
*A61B 17/3205* (2006.01)
*A61M 1/00* (2006.01)
*A61B 17/32* (2006.01)

(52) U.S. Cl.
CPC .......... *A61B 17/3205* (2013.01); *A61B 17/32* (2013.01); *A61M 1/0035* (2014.02); *A61M 1/0039* (2013.01); *A61M 1/0058* (2013.01); *A61M 1/0064* (2013.01); *A61M 1/0084* (2013.01); *A61B 2017/320008* (2013.01); *A61B 2217/005* (2013.01); *A61B 2217/007* (2013.01)

(58) Field of Classification Search
CPC ................ A61B 17/3205; A61B 17/32; A61B 17/32037; A61B 2017/3425; A61B 2017/3454; A61B 2017/32004; A61B 2017/32008; A61B 2017/22079; A61B 2217/005; A61B 2217/007; A61B 2017/320008; A61B 17/320708; A61B 2017/320004; A61B 17/32075; A61B 2017/00761; A61M 1/0035; A61M 3/0283; A61M 25/0014; A61M 1/0058; A61M 1/0064; A61M 1/0039; A61F 2002/30686

See application file for complete search history.

(56) References Cited

U.S. PATENT DOCUMENTS

| | | | | |
|---|---|---|---|---|
| 1,749,919 A | * | 3/1930 | Mierley | A61B 17/320708 606/84 |
| 2,715,899 A | * | 8/1955 | Maclean | A61B 17/320708 600/571 |
| 3,506,010 A | * | 4/1970 | Murr | A61M 1/008 604/151 |
| 3,589,363 A | * | 6/1971 | Banko | A61M 1/0064 604/22 |
| 3,955,579 A | * | 5/1976 | Bridgman | A61B 10/04 604/128 |
| 4,708,717 A | | 11/1987 | Deane et al. | |
| 4,800,896 A | * | 1/1989 | Jalowayski | A61B 10/04 600/572 |
| 4,832,683 A | * | 5/1989 | Idemoto | A61B 17/320068 604/22 |
| 5,147,292 A | | 9/1992 | Kullas et al. | |
| 5,226,426 A | * | 7/1993 | Yoon | A61B 10/0233 600/566 |

(Continued)

*Primary Examiner* — Adam Marcetich
(74) *Attorney, Agent, or Firm* — Parsons Behle & Latimer (57) ABSTRACT

A medical suction apparatus may include a wand having a proximal end and a distal end. The apparatus may further include a lumen defined within the wand, the lumen configured to couple to a suction source. The apparatus may also include a mouth defined at the distal end of the wand and placing the lumen in communication with an exterior of the wand, where the mouth has an upper edge and a lower edge, where the mouth is elongated horizontally between the upper edge and the lower edge, and where at least the upper edge or the lower edge is beveled to enable scraping of a surface.

16 Claims, 6 Drawing Sheets

(56) References Cited

U.S. PATENT DOCUMENTS

| | | | |
|---|---|---|---|
| 5,380,277 A | 1/1995 | Phillips | |
| 5,487,649 A * | 1/1996 | Dorsey, III | F04B 43/06 417/395 |
| 5,827,218 A | 10/1998 | Nguyen et al. | |
| 6,280,415 B1 * | 8/2001 | Johnson | A61B 17/0218 433/91 |
| 6,485,452 B1 | 11/2002 | French et al. | |
| 6,635,035 B1 * | 10/2003 | Marasco | A61M 35/30 604/290 |
| 7,083,601 B1 | 8/2006 | Cosmescu | |
| 8,002,732 B2 | 8/2011 | Visconti | |
| 8,100,782 B2 | 1/2012 | Craine | |
| 8,597,288 B2 | 12/2013 | Christian | |
| 8,672,928 B2 | 3/2014 | Liu et al. | |
| 9,259,519 B2 | 2/2016 | Fedenia et al. | |
| 9,314,554 B2 | 4/2016 | Orlandi | |
| 9,427,504 B2 | 8/2016 | Newman, Jr. | |
| 9,629,647 B2 * | 4/2017 | Smith | A61B 17/320016 |
| 2004/0014002 A1 * | 1/2004 | Lundgren | A61C 17/08 433/91 |
| 2004/0243157 A1 * | 12/2004 | Connor | A61M 1/0084 606/159 |
| 2005/0080411 A1 * | 4/2005 | Ouchi | A61B 18/1492 606/45 |
| 2005/0084395 A1 * | 4/2005 | Kang | A61M 3/0283 417/392 |
| 2005/0171467 A1 | 8/2005 | Landman | |
| 2007/0055282 A1 * | 3/2007 | Muschler | A61B 17/32002 606/92 |
| 2007/0149975 A1 * | 6/2007 | Oliver | A61B 17/32002 606/79 |
| 2007/0287934 A1 * | 12/2007 | Babaev | A61B 17/320068 601/2 |
| 2008/0004649 A1 * | 1/2008 | Babaev | A61B 17/320068 606/167 |
| 2008/0045986 A1 * | 2/2008 | To | A61B 17/320708 606/159 |
| 2008/0058586 A1 * | 3/2008 | Karpiel | A61B 1/00089 600/104 |
| 2008/0183200 A1 * | 7/2008 | Babaev | A61B 17/320068 606/169 |
| 2008/0249553 A1 * | 10/2008 | Gruber | A61B 17/32002 606/171 |
| 2009/0062788 A1 * | 3/2009 | Long | A61B 18/14 606/41 |
| 2009/0192442 A1 * | 7/2009 | Ignon | A61M 35/003 604/22 |
| 2010/0203470 A1 * | 8/2010 | Sidhu | A61C 17/08 433/92 |
| 2010/0262073 A1 * | 10/2010 | Henniges | A61M 3/0258 604/82 |
| 2011/0224600 A1 | 9/2011 | Orlandi | |
| 2013/0211321 A1 * | 8/2013 | Dubois | A61M 13/00 604/26 |
| 2013/0238006 A1 * | 9/2013 | O'Neil | A61B 17/32 606/170 |
| 2015/0080896 A1 * | 3/2015 | To | A61B 17/320016 606/79 |
| 2015/0105791 A1 * | 4/2015 | Truckai | A61B 17/32002 606/115 |
| 2015/0335482 A1 * | 11/2015 | Akahoshi | A61F 9/00745 604/22 |
| 2016/0081710 A1 * | 3/2016 | Barnes | A61B 17/320016 606/170 |
| 2016/0106468 A1 * | 4/2016 | Jansen | A61B 17/54 606/131 |
| 2016/0183962 A1 * | 6/2016 | Spitz | A61B 1/05 600/104 |
| 2017/0007284 A1 * | 1/2017 | Georgi | A46B 15/0081 |

* cited by examiner

CHEST CAVITY SUCTION MEDICAL APPARATUS AND METHOD

FIELD OF THE DISCLOSURE

The disclosure relates generally to medical suction apparatuses and more particularly to a chest cavity suction and scraping apparatus.

BACKGROUND

Video-assisted thoracoscopic surgical procedures enable surgeons to perform complex lung and chest cavity operations while minimizing intrusion into the body. These less invasive procedures reduce the risk of infection and speed up recovery times. One such procedure includes removing debris, such as retained hemothorax, empyema, and fibrinous exudate from a pleural space of a patient. In order to remove the debris, a camera device may be inserted through a first incision. A suction device may likewise be inserted through a second incision and used to suction the debris. Additional, instruments may also be inserted into the chest cavity through one or more additional incisions.

Typical suction devices have a small opening for suction and are not equipped to handle significant amounts of debris. For example, typical suction devices may become clogged by the debris as it enters the devices. Further, in order to remove the debris from a soft biological surface, such as a lung or chest cavity wall, a surgeon must typically insert a separate instrument into the pleural cavity to perform scraping. Alternatively, a surgeon may, for example, remove a detachable tip from a typical suction device and scrape the debris from the soft biological surface with a threaded opening of the suction device. However, the threaded openings of typical suction devices are not intended to be used in this way and may not have an edge designed for scraping purposes. Other disadvantages of typical suction devices may exist.

SUMMARY

Disclosed is a suction device that overcomes at least one of the disadvantages stated above. The suction device may include a beveled edge to enable scraping of soft biological tissue to remove attached debris without harming the tissue itself. The suction device may further have an elongated opening, or mouth, to better receive the debris. A grate at the opening may partition, or trim, the debris to facilitate suction without clogging. The suction device may further couple to an irrigation source to enable a surgeon to apply turbulent irrigation to the debris to loosen it from the tissue.

In an embodiment, a medical suction apparatus includes a wand having a proximal end and a distal end. The apparatus further includes a lumen defined within the wand, the lumen configured to couple to a suction source. The apparatus also includes a mouth defined at the distal end of the wand and placing the lumen in communication with an exterior of the wand, where the mouth has an upper edge and a lower edge, where the mouth is elongated horizontally between the upper edge and the lower edge, and where at least the upper edge or the lower edge is beveled to enable scraping of a surface.

In some embodiments, the lumen is further configured to couple to an irrigation source. In some embodiments, the lumen has a diameter of at least 10 mm to enable blood clot and fibrinous exudate debris to pass therethrough. In some embodiment, the apparatus includes a grate between the mouth and the lumen, the grate configured to partition debris passing through the mouth to prevent clogging of the lumen. In some embodiments, the upper edge of the mouth is concave and the lower edge of the mouth is flat. In some embodiments, the mouth has a crescent shape, the upper edge and the lower edge of the mouth being concave in a same direction. In some embodiments, the upper edge of the mouth is beveled to enable scraping of a surface when the wand is pulled in a backward direction. In some embodiments, the lower edge of the mouth is beveled to enable scraping of a surface when the wand is pushed in a forward direction. In some embodiments, the apparatus includes a lip on an upper portion of the distal end of the wand, the lip forming the upper edge of the mouth. In some embodiments, the apparatus includes a valve for adjusting a suction strength within the lumen.

In an embodiment, a method for applying medical suction includes applying suction to a lumen defined within a wand, the wand having a proximal end and a distal end, the wand further having an elongated mouth defined at the distal end of the wand, the mouth placing the lumen in communication with an exterior of the wand. The method further includes scraping biological debris from a biological surface with a beveled edge of the mouth. The method also includes receiving the biological debris through the lumen.

In some embodiments, the method includes applying irrigation through the lumen before applying suction to the lumen. In some embodiments, the biological debris include blood clot and fibrinous exudate debris. In some embodiments, the method includes partitioning the biological debris at a grate positioned between the mouth and the lumen. In some embodiments, the beveled edge includes an upper edge of the mouth, where scraping biological debris from the biological surface includes pulling the wand in a backward direction. In some embodiments, the beveled edge includes a lower edge of the mouth, where scraping biological debris from the biological surface includes pushing the wand in a forward direction. In some embodiments, the biological surface is a surface of a lung or a surface of a pleural cavity wall. In some embodiments, the method includes adjusting a suction strength within the lumen.

In an embodiment, a medical suction device includes a wand having a proximal end and a distal end. The device further includes a lumen defined within the wand, the lumen configured to couple to a suction source. The device also includes a mouth defined at the distal end of the wand and placing the lumen in communication with an exterior of the wand, where the mouth has a beveled edge to enable scraping of a biological surface. In some embodiments, the device includes a grate positioned between the mouth and the lumen, the grate configured to partition biological debris passing through the mouth to prevent clogging of the lumen.

While the disclosure is susceptible to various modifications and alternative forms, specific embodiments have been shown by way of example in the drawings and will be described in detail herein. However, it should be understood that the disclosure is not intended to be limited to the particular forms disclosed. Rather, the intention is to cover all modifications, equivalents and alternatives falling within the scope of the disclosure.

DETAILED DESCRIPTION

Figure 1A:
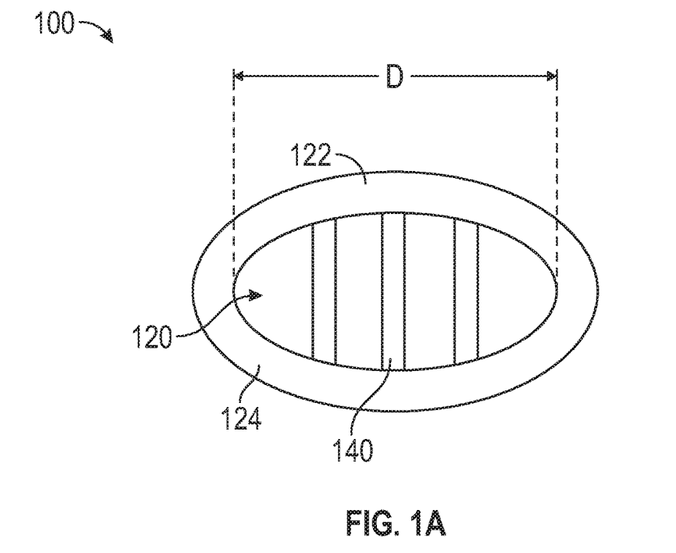
FIGS. 1A and 1B are a schematic front and side view, respectively, depicting an embodiment of a medical suction apparatus with an elongated mouth.
Figure 1B:
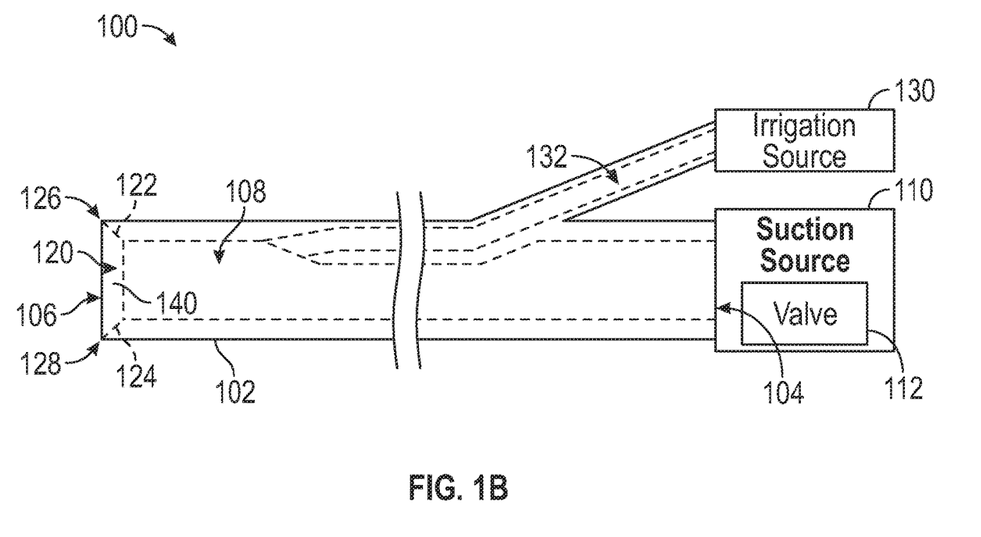

Referring to FIGS. 1A and 1B, an embodiment of a medical suction apparatus 100 is depicted. FIG. 1A depicts a front view of the apparatus 100 and FIG. 1B depicts a side view of the apparatus 100. The apparatus 100 may be used for video-assisted thoracoscopic surgical procedures. For clarity purposes, a length of the apparatus 100 has been condensed in FIG. 1B. In practice, the length of that apparatus 100 would be sufficient to enable a surgeon to grasp the apparatus 100 while inserting a portion of the apparatus 100 through an incision into a chest cavity of a patient. Likewise, proportions of the various features of the apparatus 100 have been modified for description purposes.

The apparatus 100 may include a wand 102 having a proximal end 104 and a distal end 106. The wand 102 may have a lumen 108 defined therein. The lumen 108 may provide suction and irrigation during a surgical procedure. For example, the lumen 108 may be configured to couple to a suction source 110. The suction source 110 may include a valve 112 for adjusting a strength of the suction through the lumen 108. The apparatus 100 may be further configured to couple to an irrigation source 130. An irrigation channel 132 may attach to the irrigation source 130 and introduce irrigation into the lumen 108. The suction and irrigation may be used to loosen and remove debris, such as blood clot debris and/or fibrinous exudate debris, from within a chest cavity.

The wand 102 may further have a mouth 120 defined therein at the distal end 106 of the wand 102. The mouth 120 may place the lumen 108 in communication with an exterior of the wand 102. A grate 140 may be positioned between the mouth 120 and the lumen 108 to partition, or trim, debris as it passes into the lumen 108. By partitioning the debris, the grate 140 may prevent and/or reduce the chance of clogging of the lumen 108.

The mouth 120 may have an upper edge 122 and a lower edge 124. The mouth 120 may further be elongated horizontally between the upper edge 122 and the lower edge 124 as depicted in FIG. 1A. At least one of the upper edge 122 or the lower edge 124 or both may be beveled to enable scraping of a biological surface. As depicted in FIG. 1B, the upper edge 122 is beveled to form a first scraping edge 126 and the lower edge 124 is also beveled to form a second scraping edge 128.

As depicted in FIG. 1A, in some embodiments the mouth may have an elliptical or oval shape with the upper edge 122 being concave down and the lower edge 124 being concave up. Further, the mouth 120 may have a major axis length, denoted by the distance D, of at least 10 mm to enable debris, such as blood clot debris and/or fibrinous exudate debris, to pass therethrough. The lumen 108 may also have a diameter of at least 10 mm to enable debris to pass therethrough.

During operation, suction may be applied to the lumen 108 by the suction source 110. The strength of the suction may be adjusted using the valve 112. Further, irrigation may be introduced into the lumen 108 using the irrigation source 130. The irrigation may be applied either prior to the suction or simultaneously with the suction. The irrigation may loosen debris to be suctioned through the lumen 108.

While suction is being applied, a user may scrape debris from a surface using either the first scraping edge 126 or the second scraping edge 128. For example, the surface may include a surface of a lung or a surface of a pleural cavity wall. The debris may include blood clot debris, fibrinous exudate debris, or both. The debris may be received through the lumen 108 and eventually discarded after reaching the suction source 110. Before being received into the lumen 108, the debris may be partitioned by the grate 140 to prevent clogging of the lumen 108.

A benefit of the apparatus 100 is that by including at least one beveled edge 126, 128 along the mouth 120, a scraping edge (either the first scraping edge 126, the second scraping edge 128, or both) may be formed to assist a surgeon in removing debris that is adhered to an internal surface of a body. Likewise, the elliptical shape of the mouth 120 may provide a better shape for scraping debris as compared to suction devices that have a round lumen defined therein. By performing the scraping at a suction device, the apparatus 100 may enable a surgery to be accomplished with the insertion of fewer tools and possibly with fewer incisions. Further, by including the grate 140 between the mouth 120 and the lumen 108, clogs within the lumen 108 may be avoided as compared to suction devices that do not include a grate for partitioning debris. Other advantages may exist.

Figure 2A:
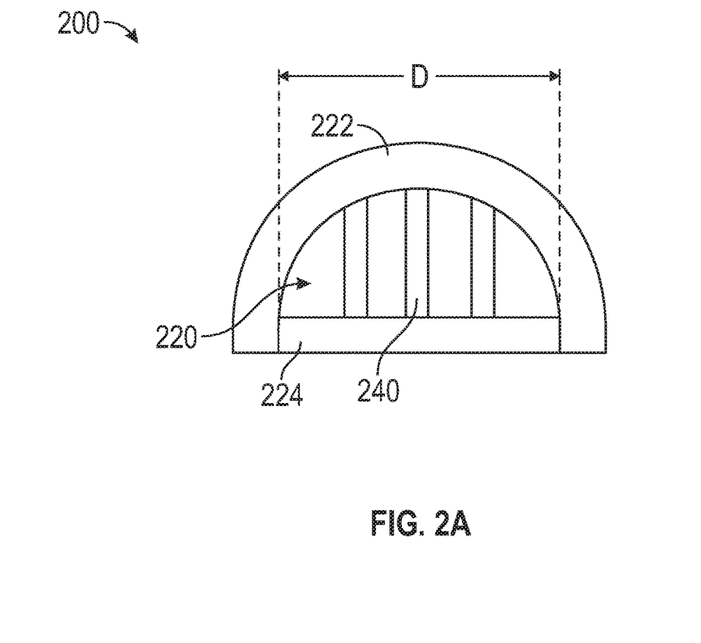
FIGS. 2A and 2B are a schematic front and side view, respectively, depicting an embodiment of a medical suction apparatus with an elongated mouth having a flat lower edge.
Figure 2B:
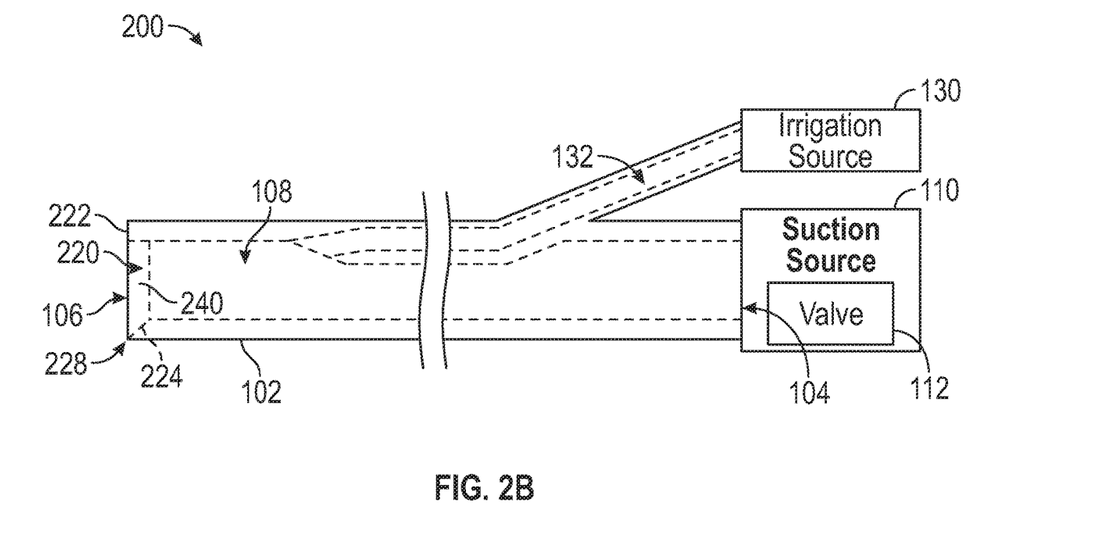

Referring to FIGS. 2A and 2B, an embodiment of a medical suction apparatus 200 is depicted. FIG. 2A depicts a front view of the apparatus 200 and FIG. 2B depicts a side view of the apparatus 200. As with the apparatus 100, the apparatus 200 may be used for video-assisted thoracoscopic surgical procedures. Length depictions and proportions of the various features of the apparatus 200 have also been modified for description purposes.

The wand 102 of the apparatus 200 may have a mouth 220 defined therein at the distal end 106 of the wand 102. The mouth 220 may place the lumen 108 in communication with an exterior of the wand 102. A grate 240 may be positioned between the mouth 220 and the lumen 108 to partition, or trim, debris as it passes into the lumen 108. By partitioning the debris, the grate 140 may prevent clogging or the lumen 108.

The mouth 220 may have an upper edge 222 and a lower edge 224. The mouth 220 may be elongated horizontally between the upper edge 222 and the lower edge 224 as depicted in FIG. 2A. Further, the lower edge 224 may be beveled to enable scraping of a surface with a scraping edge 228.

As depicted in FIG. 2A, the mouth may have a semi circle shape with the upper edge 222 being concave down and the lower edge 224 being flat. A width of the mouth 220, denoted by the distance D, may be at least 10 mm to enable debris, such as blood clot debris and/or fibrinous exudate debris, to pass therethrough. The lumen 108 may also have a diameter of at least 10 mm to enable debris to pass therethrough.

During operation, the scraping edge 228 may be used to scrape biological debris from a biological surface. A benefit of the apparatus 200 is that by having a flat lower edge 224, the scraping edge 228 may have more contact with the biological surface enabling more debris to be scraped with each pass. Other benefits and advantages may exist.

Figure 3A:
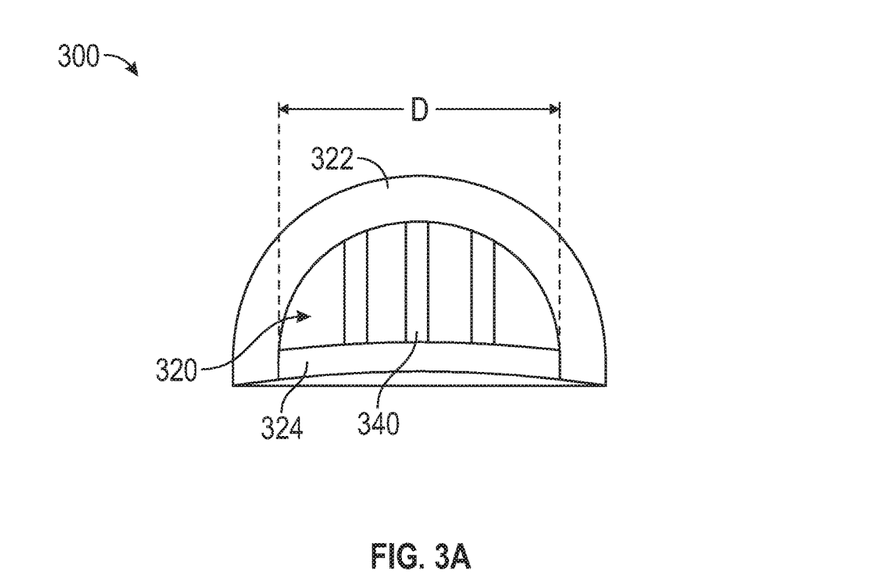
FIGS. 3A and 3B are a schematic front and side view, respectively, depicting an embodiment of a medical suction apparatus with an elongated mouth having a concave down lower edge.
Figure 3B:
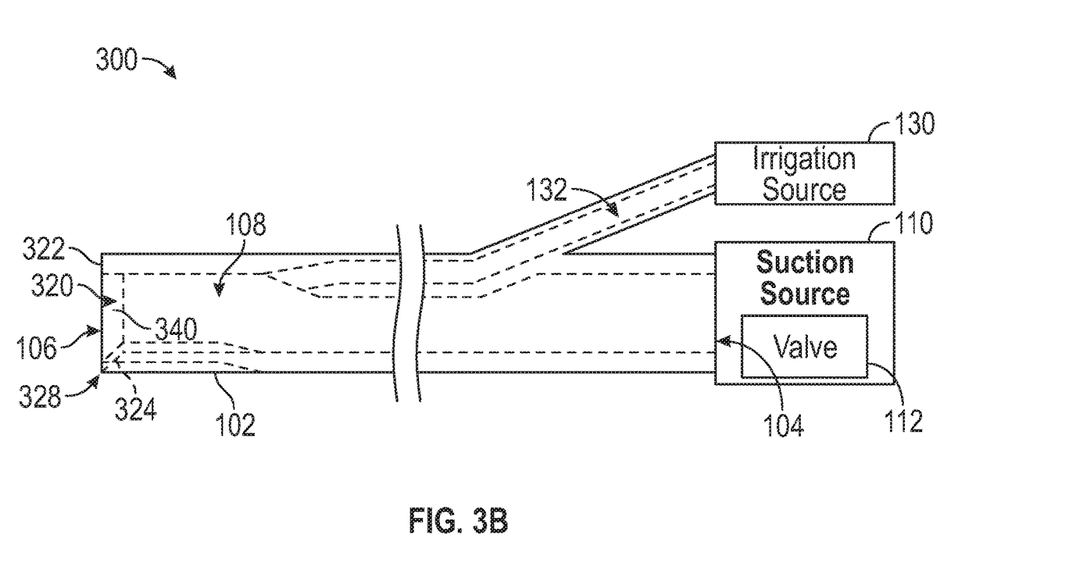

Referring to FIGS. 3A and 3B, an embodiment of a medical suction apparatus 300 is depicted. FIG. 3A depicts a front view of the apparatus 300 and FIG. 3B depicts a side view of the apparatus 300. As with the apparatuses 100, 200 the apparatus 300 may be used for video-assisted thoracoscopic surgical procedures. Length depictions and proportions of the various features of the apparatus 300 have also been modified for description purposes.

The wand 102 of the apparatus 300 may have a mouth 320 defined therein at the distal end 106 of the wand 102. The mouth 320 may place the lumen 108 in communication with an exterior of the wand 102. A grate 340 may be positioned between the mouth 320 and the lumen 108 to partition debris as it passes into the lumen 108. By partitioning the debris, the grate 340 may prevent clogging or the lumen 108.

The mouth 320 may have an upper edge 322 and a lower edge 324. The mouth 320 may be elongated horizontally between the upper edge 322 and the lower edge 324 as depicted in FIG. 3A. Further, the lower edge 324 may be beveled to enable scraping of a As depicted in FIG. 3A, the mouth may have a crescent shape with the upper edge 322 being concave down and the lower edge 324 also being concave down. A width of the mouth 320, denoted by the distance D, may be at least 10 mm to enable debris, such as blood clot debris and fibrinous exudate debris, to pass therethrough. The lumen 108 may also have a diameter of at least 10 mm to enable debris to pass therethrough.

During operation, the scraping edge 328 may be used to scrape biological debris from a biological surface. A benefit of the apparatus 300 is that by having a concave down lower edge 324, the scraping edge 328 may have a shape the more closely fits the biological surface. For example, a lung may have a rounded exterior that corresponds to a shape of the lower edge 324. The shape may enable more debris to be scraped with each pass and reduce the risk of harm to the biological surface. Other benefits and advantages may exist.

Figure 4A:
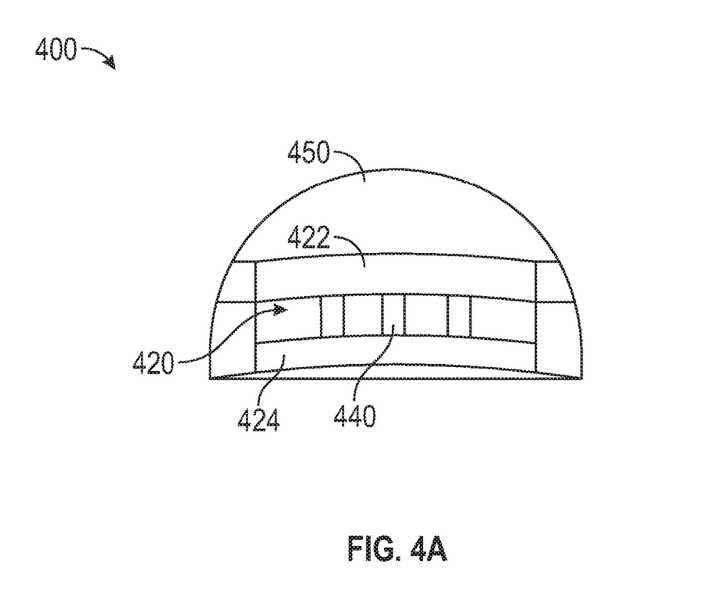
FIGS. 4A and 4B are a schematic front and side view, respectively, depicting an embodiment of a medical suction apparatus with an elongated mouth and having an upper lip forming an upper edge of the elongated mouth.
Figure 4B:
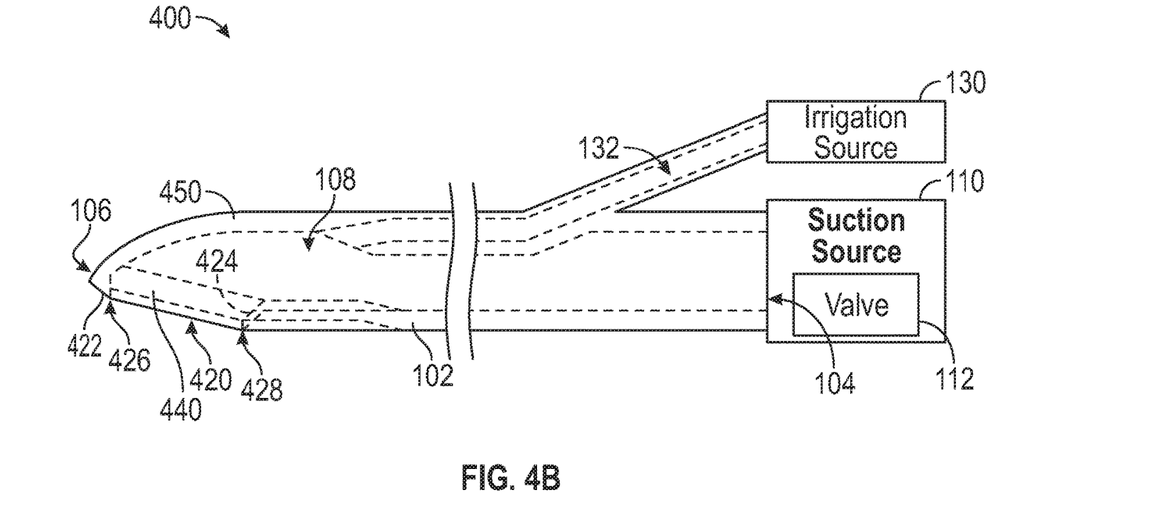

Referring to FIGS. 4A and 4B, an embodiment of a medical suction apparatus 400 is depicted. FIG. 4A depicts a front view of the apparatus 400 and FIG. 4B depicts a side view of the apparatus 400. As with the apparatuses 100, 200, 300 the apparatus 400 may be used for video-assisted thoracoscopic surgical procedures. Length depictions and proportions of the various features of the apparatus 400 have also been modified for description purposes.

The wand 102 of the apparatus 400 may have a mouth 420 defined therein at the distal end 106 of the wand 102. As used herein, the phrase "at the distal end" means being closer to the distal end than the proximal end 104. The mouth 420 may place the lumen 108 in communication with an exterior of the wand 102. A grate 440 may be positioned between the mouth 420 and the lumen 108 to partition, or trim, debris as it passes into the lumen 108. By partitioning the debris, the grate 440 may prevent clogging or the lumen 108.

The mouth 420 may have an upper edge 422 and a lower edge 424. The mouth 420 may further be elongated horizontally between the upper edge 422 and the lower edge 424 as depicted in FIG. 4A. The apparatus 400 may further include a lip 450 covering an upper portion of the mouth 420. The lip 450 may form the upper edge 422. As such, the mouth 420 may be positioned on an underside of the wand 102 with a slight incline as shown in FIG. 4B.

The upper edge 422 of the mouth 420 may be beveled to enable scraping of a surface by pulling the apparatus 400 in a backward direction (e.g., from left to right in FIG. 4B). For example, the upper edge 422 may be beveled to create a backward facing scraping edge 426. The lower edge 424 of the mouth 420 may be beveled to enable scraping of a surface by pushing the apparatus 400 in a forward direction (e.g., from right to left in FIG. 4B). For example, the lower edge 424 may be beveled to create a forward facing scraping edge 428.

The mouth 420 may have a crescent shape with the upper edge 422 being concave down and the lower edge 424 also being concave down. A width of the mouth 420 may be at least 10 mm to enable debris, such as blood clot debris and/or fibrinous exudate debris, to pass therethrough. The lumen 108 may also have a diameter of at least 10 mm to enable debris to pass therethrough.

During operation, suction and irrigation may be applied and adjusted at the apparatus 400 as described herein. While suction is being applied, a user may scrape biological debris from a soft biological surface using either the first scraping edge 426 or the second scraping edge 428. A user may tilt the apparatus 400 forward and pull it back to scrape with the first scraping edge 426. A user may tilt the apparatus 400 backward and push it forward to scrape with the second scraping edge 428. The biological debris may be received through the lumen 108 and eventually discarded after reaching the suction source 110. Before being received into the lumen 108, the debris may be partitioned by the grate 440 to prevent clogging of the lumen 108.

A benefit of the apparatus 400 is that the first scraping edge 426 may enable the apparatus 400 to scrap soft biological tissue by pulling the apparatus 400 backward as well as pushing the apparatus 400 forward as opposed to typical scraping devices that only allow scraping in one direction. Other benefits may exist.

Figure 5A:
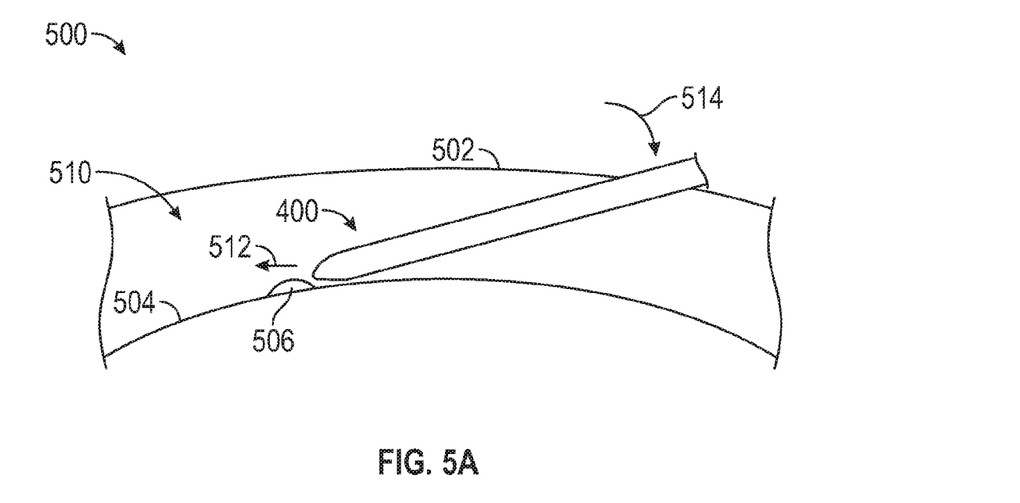
FIGS. 5A and 5B are diagrams depicting use of an embodiment of a medical suction device in a first direction and second direction respectively.

Referring to FIG. 5A, use of the embodiment of the apparatus 400 within a body 500 is depicted. The apparatus 400 may be inserted through a first surface 502 through an incision (not shown) and pass into a cavity 510 (e.g., a pleural cavity). The first surface 502 may be an exterior wall of the cavity 510. The apparatus 400 may be placed in contact with a second surface 504 within the cavity 510. The second surface 504 may be a biological surface, such as a surface of a lung, a surface of a pleural cavity wall, or a surface of another internal organ or structure of the body 500.

While inserted into the cavity 510, the apparatus 400 may be used to irrigate and suction a portion of the second surface 504 in order to remove biological debris 506 from the second surface 504. As explained herein, the biological debris 506 may include blood clot and/or fibrinous exudate debris. The apparatus 400 may further be used to scrape the biological debris 506 from the second surface 504. The apparatus 500 may include a scraping edge along a lower edge of the apparatus 400 to enable scraping by holding the apparatus 400 at a lower angle, as depicted by the arrow 514, and moving the apparatus 400 along the surface 504 in a forward direction, as depicted by the arrow 512.

Figure 5B:
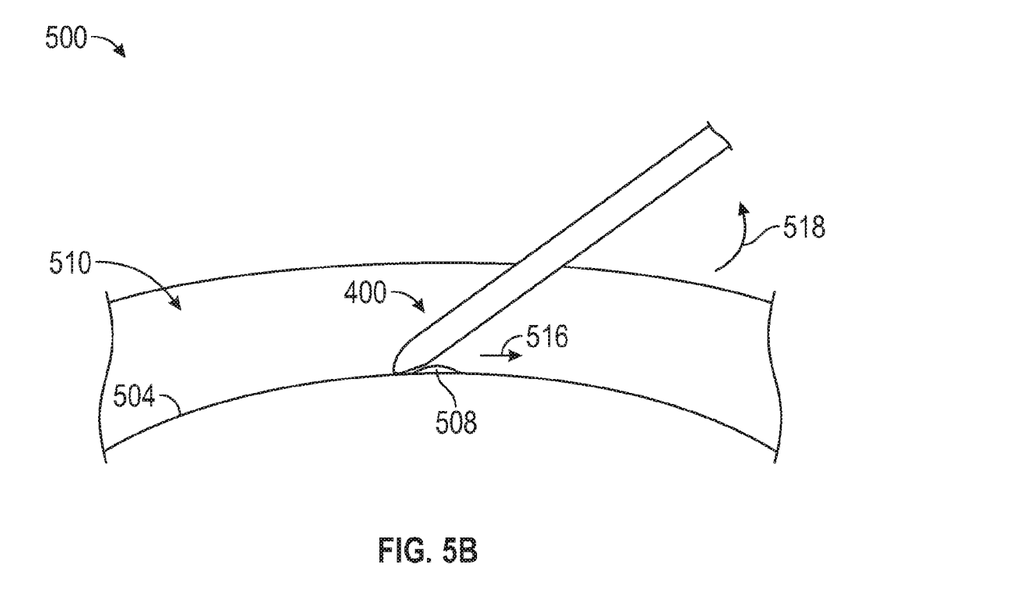

Referring to FIG. 5B, the apparatus 400 may further be used for scraping by holding the apparatus 400 at a higher angle, as depicted by the arrow 518, and pulling the apparatus 400 along the surface 504 in a backward direction, as depicted by the arrow 516.

Figure 6:
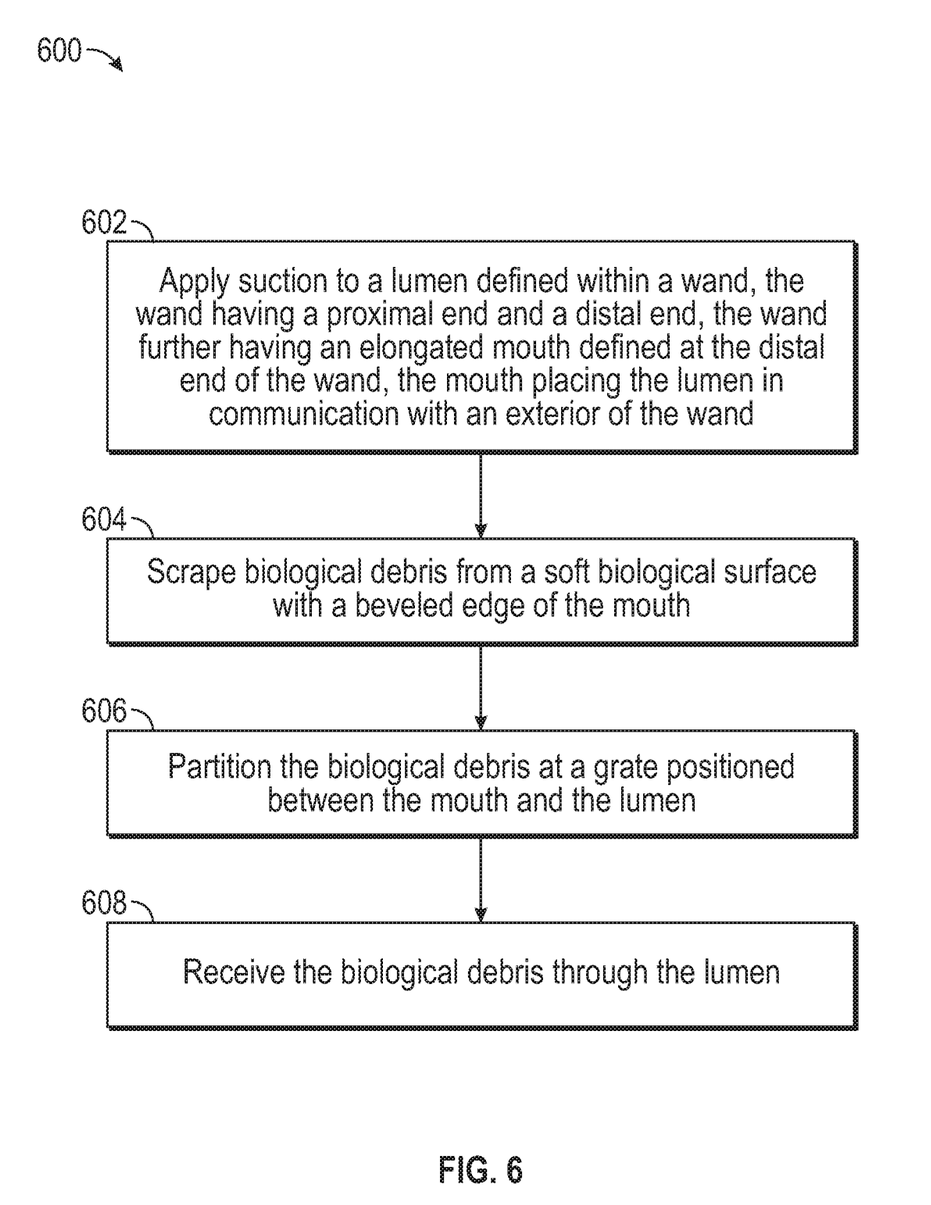
FIG. 6 is a flow chart depicting an embodiment of a method of for applying medical suction.

Referring to FIG. 6, an embodiment of a method of applying medical suction is depicted. The method 600 may include applying suction to a lumen defined within a wand, the wand having a proximal end and a distal end, the wand further having an elongated mouth defined at the distal end of the wand, the mouth placing the lumen in communication with an exterior of the wand, at 602. For example, suction may be applied to the lumen 108 of the apparatuses 100, 200, 300, 400.

The method may further include scraping biological debris from a biological surface with a beveled edge of the mouth, at 604. For example, the biological debris 506 or the biological debris 508 may be scraped from the second surface 504.

The method may also include partitioning the biological debris at a grate positioned between the mouth and the lumen, at 606. For example, the biological debris may be partitioned at one of the grates 140, 240, 340, 440.

The method may include receiving the biological debris through the lumen, at 608. For example, biological debris 506 or the biological debris 508 may be received through the lumen 108.

A benefit of the method 600 is that a surgeon may remove debris that is adhered to an internal surface of a body using a scraping edge that is less likely to harm soft biological tissue, such as a lung. The method may further enable a surgery to be accomplished with the insertion of fewer tools and possibly with fewer incisions. Also, clogs within the lumen may be avoided as compared to suction devices that do not include a grate for partitioning debris. Other advantages may exist.

Although various embodiments have been shown and described, the present disclosure is not so limited and will be understood to include all such modifications and variations as would be apparent to one skilled in the art.

What is claimed is:

1. A medical suction apparatus comprising:
   a wand having a proximal end and a distal end;
   a lumen defined within the wand, the lumen configured to couple to a suction source;
   a mouth defined within a single integral wall of a single tube at the distal end of the wand and placing the lumen in communication with an exterior of the wand, wherein the mouth has an upper edge at the distal end of the wand and a lower edge closer to the proximal end than the distal end, wherein the upper edge includes a backward facing scraping edge to enable scraping of biological debris from a surface of soft biological tissue without harming the soft biological tissue when the wand is pulled in a backward direction, and wherein the lower edge includes a forward facing scraping edge to enable scraping of biological debris from a surface of soft biological tissue without harming the soft biological tissue when the wand is pushed in a forward direction.

2. The apparatus of claim 1, wherein the lumen is further configured to couple to an irrigation source.

3. The apparatus of claim 1, wherein the lumen has a diameter of at least 10 mm to enable blood clot and fibrinous exudate debris to pass therethrough.

4. The apparatus of claim 1, further comprising a grate between the mouth and the lumen, the grate configured to partition debris passing through the mouth to prevent clogging of the lumen.

5. The apparatus of claim 1, wherein the upper edge is concave and the lower edge is flat.

6. The apparatus of claim 1, wherein the mouth has a crescent shape, the upper edge and the lower edge of the mouth being concave in a same direction.

7. The apparatus of claim 1, further comprising a lip on an upper portion of the distal end of the wand, the lip forming the upper edge of the mouth.

8. The apparatus of claim 1, further comprising a valve for adjusting a suction strength within the lumen.

9. A method for applying medical suction comprising:
   applying suction to a lumen defined within a wand, the wand having a proximal end and a distal end, the wand further having mouth having a first edge defined at the distal end of the wand and a second edge closer to the proximal end than the distal end, wherein the first edge includes a backward facing scraping edge, wherein the second edge includes a forward facing scraping edge and, wherein where the mouth places the lumen in communication with an exterior of the wand, wherein the first edge and the second edge enable scraping of biological debris from a surface of soft biological tissue without harming the soft biological tissue;
   scraping the biological debris from the surface of the biological tissue with the first edge of the mouth when the wand is tilted to an angle that places the first edge of the mouth in contact with the biological surface while the second edge of the mouth is not in contact with the biological surface and the wand is pulled in a backward direction;
   scraping the biological debris from the surface of the biological tissue with the second edge of the mouth when the wand is tilted to an angle that places the second edge of the mouth in contact with the biological surface while the first edge of the mouth is not in contact with the biological surface and the wand is pushed in a forward direction; and
   receiving the biological debris through the lumen.

10. The method of claim 9, further comprising applying irrigation through the lumen before applying suction to the lumen.

11. The method of claim 9, wherein the biological debris include blood clot and fibrinous exudate debris.

12. The method of claim 9, further comprising partitioning the biological debris at a grate positioned between the mouth and the lumen.

13. The method of claim 9, wherein the biological surface is a surface of a lung or a surface of a pleural cavity wall.

14. The method of claim 9, further comprising adjusting a suction strength within the lumen.

15. A medical suction device comprising:
   a wand having a proximal end and a distal end;
   a lumen defined within the wand, the lumen configured to couple to a suction source;
   a mouth defined in the wand and placing the lumen in communication with an exterior of the wand, wherein the lumen curves downward at the distal end of the wand, wherein the mouth is at an obtuse angle relative to an outer surface of the wand, and wherein the mouth includes a backward facing scraping edge to enable scraping of biological debris from a surface of soft biological tissue without harming the soft biological tissue when the wand is pulled in a backward direction, and wherein the mouth includes a forward facing scraping edge to enable scraping of biological debris from a surface of soft biological tissue without harming the soft biological tissue when the wand is pushed in a forward direction.

16. The device of claim 15, further comprising:
a grate positioned between the mouth and the lumen, the grate configured to partition biological debris passing through the mouth to prevent clogging of the lumen.

* * * * *